(12) United States Patent
Bentley et al.

(10) Patent No.: US 7,648,241 B2
(45) Date of Patent: *Jan. 19, 2010

(54) CORNEAL MEASUREMENT APPARATUS AND A METHOD OF USING THE SAME

(75) Inventors: Joseph R. Bentley, West Jordan, UT (US); Ming Lai, Webster, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/955,001

(22) Filed: Dec. 12, 2007

(65) Prior Publication Data

US 2008/0212030 A1    Sep. 4, 2008

Related U.S. Application Data

(63) Continuation-in-part of application No. 11/614,518, filed on Dec. 21, 2006, now abandoned.

(51) Int. Cl.
*A61B 3/10* (2006.01)

(52) U.S. Cl. .................. 351/214; 351/212; 351/221

(58) Field of Classification Search ............. 351/206, 351/211–212, 214
See application file for complete search history.

(56) References Cited

U.S. PATENT DOCUMENTS

| 4,376,573 | A | * | 3/1983 | Matsumura et al. ......... 351/212 |
| 4,422,736 | A |   | 12/1983 | Nunokawa |
| 5,512,965 | A |   | 4/1996 | Snook |
| 5,512,966 | A |   | 4/1996 | Snook |
| 6,286,958 | B1 |  | 9/2001 | Koest et al. |
| 6,409,346 | B1 |  | 6/2002 | Koest et al. |
| 6,575,573 | B2 |  | 6/2003 | Lai et al. |
| 6,692,126 | B1 |  | 2/2004 | Xie et al. |
| 6,729,727 | B2 | * | 5/2004 | Nanjo ...................... 351/206 |
| 7,040,765 | B2 |  | 5/2006 | Koest |
| 7,275,827 | B2 |  | 10/2007 | Jean |
| 7,284,861 | B2 | * | 10/2007 | Fujieda ..................... 351/206 |
| 7,290,879 | B2 | * | 11/2007 | Nagata et al. .............. 351/205 |
| 7,434,932 | B2 | * | 10/2008 | Hanebuchi ................. 351/206 |
| 7,506,980 | B2 | * | 3/2009 | Fujieda ..................... 351/205 |
| 2002/0036749 | A1 | * | 3/2002 | Isogai ...................... 351/206 |
| 2005/0122474 | A1 |  | 6/2005 | Koretz |
| 2005/0134797 | A1 |  | 6/2005 | Grove |
| 2005/0195360 | A1 | * | 9/2005 | Akita et al. ................ 351/212 |

* cited by examiner

*Primary Examiner*—Jordan M. Schwartz
(74) *Attorney, Agent, or Firm*—Jeffrey B. Powers (57) ABSTRACT

An apparatus for measuring a subject's cornea, comprising (A.) a slit projection subsystem comprising a light source, (B.) a mask subsystem disposed in a path of light from the light source, comprising a first slit mask defining a plurality of apertures, (C.) a movement apparatus adapted to move at least a portion of the slit projection subsystem, the movement apparatus configured and arranged such that, by moving the portion of the slit projection subsystem, portions of the light can be selectively transmitted through an aperture of the plurality of apertures toward the cornea, (D.) an imaging element configured and arranged to image at least one of the plurality of apertures onto the cornea, and (E.) an image capture subsystem arranged to capture images of the portions of light after the light impinges on the cornea.

27 Claims, 6 Drawing Sheets

CORNEAL MEASUREMENT APPARATUS AND A METHOD OF USING THE SAME

RELATED APPLICATION

This application claims priority to and is a continuation in part of U.S. patent application Ser. No. 11/614,518, entitled "Corneal Measurement Apparatus and Method of Using Same," filed on Dec. 21, 2006, now abandoned which is hereby incorporated by reference in its entirety.

FIELD OF INVENTION

The present invention relates to corneal measurement apparatus and a method of corneal measurement, and more particularly to an apparatus and method for projecting a plurality of slits of light for performing corneal measurements.

BACKGROUND OF THE INVENTION

Ophthalmologists and optometrists would like to have an accurate representation of subjects' eye. Such representations include, for example, one or more of a representation of a subject's corneal anterior surface, posterior surface, and corneal thickness and density, as well as anterior chamber profiles. This information may be used to prescribe contact lenses and eye glasses, and to reshape the cornea by surgical procedures or to perform other surgical procedures. Since it is not comfortable to measure these data with physical contact, remote sensing techniques are preferably used to perform the measurements. A device that measures only the front surface of a cornea is commonly referred to as corneal topographer, a device that measures the front and back surfaces of a cornea, and the stroma of the eye is referred to as a corneal profiler, and a device that measures anterior chamber profile including the cornea is called an anterior chamber analyzer.

One common technique for obtaining corneal measurement information includes projecting narrow bands of light (commonly referred to as slits or slit beams) onto a patient's cornea at multiple locations across a cornea. For each of the slits, after the light in the slit has been scattered by the cornea, an image of the light is obtained.

To project a slit of light, typically, an aperture of appropriate shape and size, and a lens are placed in the path of light from a light source such that the light passing through the aperture forms a slit of light on a subject's cornea. Typically, to project slits at each of multiple locations across the cornea, a single aperture is translated such that the light passing through the aperture at selected times forms the multiple slits. One example of such a corneal measurement apparatus is presented in U.S. Pat. No. 5,512,966 to Snook.

A problem with such apparatus is that it is difficult to accurately position an aperture to form each of the slits, and over time (after many patients) it is difficult to know the position of the slits accurately so that an accurate recreation of a cornea can be obtained.

SUMMARY

Aspects of the present invention are directed to eye measurement apparatus having a slit mask defining a plurality of apertures for projecting slits of light onto an eye.

An aspect of the present is directed to an apparatus for measuring a subject's cornea, comprising (A.) a slit projection subsystem comprising a light source, (B.) a mask subsystem disposed in a path of light from the light source, comprising a first slit mask defining a plurality of apertures, (C.) a movement apparatus adapted to move at least a portion of the slit projection subsystem, the movement apparatus configured and arranged such that, by moving the portion of the slit projection subsystem, portions of the light can be selectively transmitted through an aperture of the plurality of apertures toward the cornea, (D.) an imaging element configured and arranged to image at least one of the plurality of apertures onto the cornea, and (E.) an image capture subsystem arranged to capture images of the portions of light after the light impinges on the cornea.

In some embodiments, the slit projection subsystem comprises a second slit mask defining a selection aperture, the movement apparatus being adapted to move the second slit mask.

In some embodiments, the apparatus further comprises (F.) a second slit projection subsystem comprising a second light source, (G.) a second mask subsystem disposed in a path of second light from the second slit projection subsystem, comprising a second slit mask defining a second plurality of apertures, (H.) a second movement apparatus adapted to move at least a portion of the second slit projection subsystem, the second movement apparatus configured and arranged such that by moving the portion of the second slit projection subsystem, portions of the second light can be selectively transmitted through an aperture of the second plurality of apertures toward the cornea; and (I.) a second imaging element configured and arranged to image the second plurality of apertures onto the cornea, the image capture subsystem arranged to capture images of the portions of second light after the light impinges on the cornea.

In some embodiments, the second slit mask is disposed upstream of the first slit mask. In some embodiments, the slit projection subsystem is configured and arranged to project light from the light source through each of the plurality of apertures defined in first slit mask without moving the light source.

In some embodiments, the light source comprises at least one LED arranged to project light in the path of light. In some embodiments, the apparatus further comprises a condenser lens configured and arranged to gather light from the light source and project the light in the path of light. In some embodiments, the imaging element and condenser lens are configured and arranged to operate as a condenser-projector system. In some embodiments, the imaging element and the first slit mask are disposed in a Scheimpflug arrangement to obtain a plane of slit images at the cornea.

In some embodiments, the plurality of apertures is disposed in a single plane. In some embodiments, the plurality of apertures is formed on a single substrate. In some embodiments, the plurality of apertures is defined by openings in an opaque layer deposited on the substrate.

In some embodiments, the apparatus comprises an image processing subsystem coupled to the image capture subsystem, the image processing subsystem being adapted to convert the images into a representation of the cornea. In some embodiments, the apparatus further comprises a subject positioning apparatus adapted to maintain the subject's cornea in a location.

In some embodiments, the light source comprises at least one high power LED. In some embodiments, the light source consists of a single LED.

In some embodiments, the movement apparatus is adapted to translate the at least portion of the slit projection subsystem. In some embodiments, the light source is adapted to project a slit of light and the movement apparatus is adapted to translate the light source. In some embodiments, the movement apparatus is adapted to translate the second slit mask. In some embodiments, the movement apparatus is adapted to rotate the at least portion of the slit projection subsystem.

Another aspect of the present invention is directed to a method of facilitating measurement of a subject's cornea, comprising: (A.) providing a plurality of apertures, (B.) projecting light toward the plurality of apertures, (C.) moving at least a portion of a slit projector subsystem while maintaining the plurality of apertures in fixed locations to selectively transmit a portion of the light toward the cornea, the portion of the light passing through a selected aperture of the plurality of apertures; and, (D.) imaging the portions of light after the light impinges on the cornea.

In some embodiments, the step of moving comprises translating the at least portion of the slit projection subsystem. In some embodiments, the step of moving comprises rotating the at least portion of the slit projection subsystem.

In some embodiments, the step of moving comprises moving a selection slit. In some embodiments, the step of moving comprises moving at least one source.

In some embodiments, the light passes through the selection aperture prior to passing through any of the plurality of apertures. In some embodiments, the step of projecting light comprises projecting light from at least one LED. In some embodiments, the step of imaging produces images, and the method further comprises processing the images to convert the images into a representation of the cornea.

BRIEF DESCRIPTION OF THE DRAWINGS

Illustrative, non-limiting embodiments of the present invention will be described by way of example with reference to the accompanying drawings, in which the same reference number is used to designate the same or similar components in different figures, and in which.

DETAILED DESCRIPTION

Figure 1:
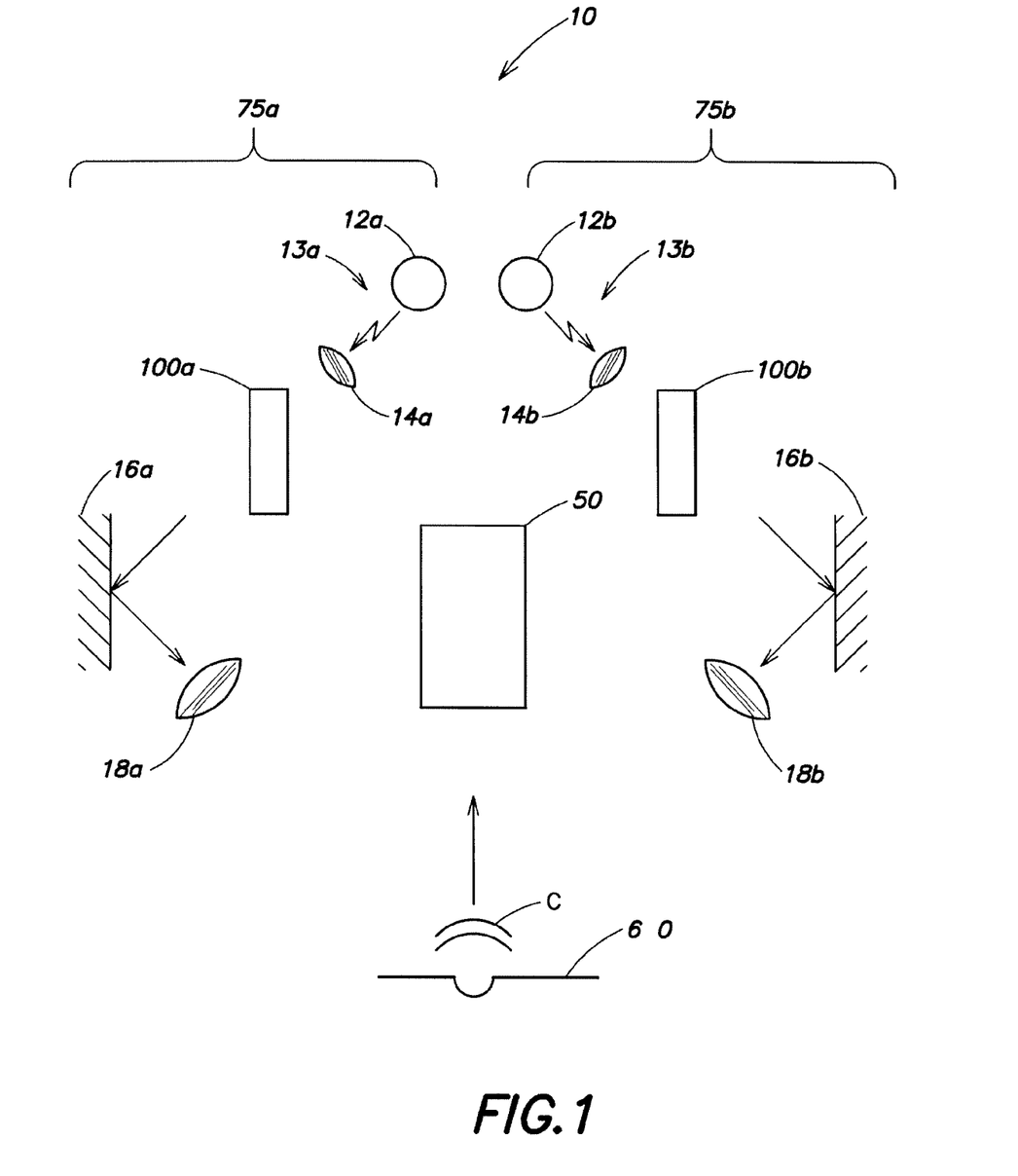
FIG. 1 is a schematic view of an example of a corneal measurement apparatus according to aspects of the present invention.

FIG. 1 is a schematic view of an embodiment of a corneal measurement apparatus 10 according to aspects of the present invention. The corneal measurement apparatus is adapted to measure a subject's cornea C. The corneal measurement apparatus comprises two slit projection systems 13a, 13b (including light sources 12a and 12b, respectively), two mask subsystems 100a, 100b, and an image capture subsystem 50. Mask subsystems 100a and 100b are disposed in the paths of light from slit projection systems 13a and 13b, respectively.

Slit projection system 13a and mask subsystem 100a are in a first arm 75a of the corneal measurement apparatus and slit projection system 13b and mask subsystem 100b are in a second arm 75b of the corneal measurement apparatus. In the illustrated embodiment, the first arm projects slits of light onto one half of the cornea, and the second arm projects slits of light onto the other half of the cornea. For example, the path of each of the projected slits of light may be at a approximately forty-five degree angle to the visual axis of the subject's eye. Although the illustrated embodiment of a measurement apparatus has two arms, in other embodiments, a measurement apparatus may only have a single arm.

Figure 2:
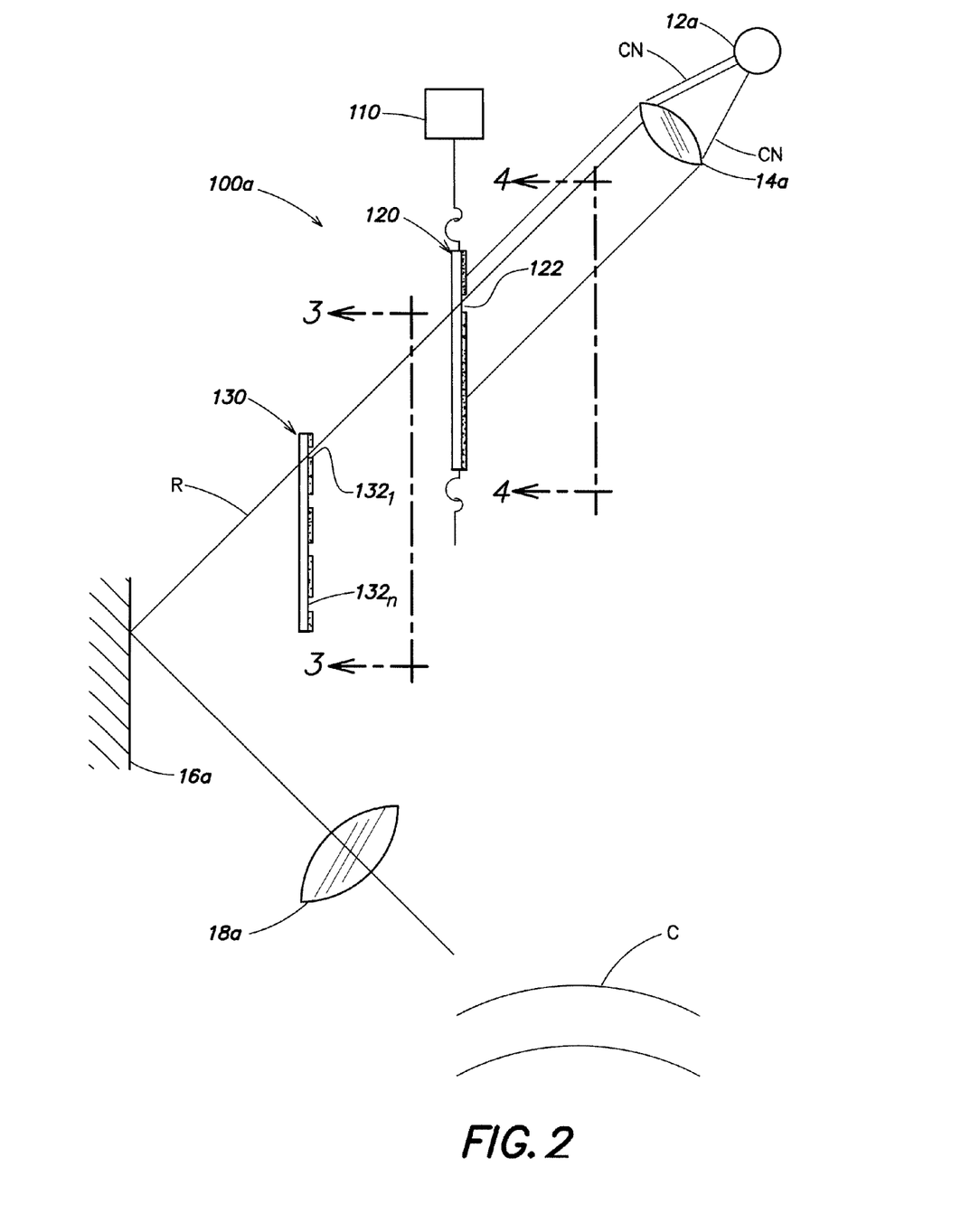
FIG. 2 is an expanded view showing further details of one arm of the corneal measurement apparatus of FIG. 1.

Referring to FIG. 2, further details of an example embodiment of one arm of the corneal measurement apparatus 10 are shown. The arm comprises a mask subsystem comprising a first slit mask 130 defining a plurality of apertures $132_i$ and a slit projection subsystem comprising a light source 12a and a second slit mask 120 defining a selection aperture 122.

The arm also comprises a movement apparatus 110 adapted to translate the second mask. Second slit mask 120 is configured and arranged such that, by appropriately positioning the second slit mask using the movement apparatus to move the second slit mask relative to the first slit mask, selection aperture 122 selectively transmits portions of the light from source 12a such that light traveling through an aperture of the plurality of apertures $132_i$ impinges on cornea C. It will be appreciated that although in the illustrated embodiment, the movement apparatus translates the second mask, the movement apparatus may move the selection aperture in any suitable manner to suitably position the selection aperture. Also, the movement apparatus may move any suitable portion of the slit projection subsystem to suitably project a slit of light onto a cornea C. For example, as set forth below, the light source may be moved.

Ray R demonstrates that the selection aperture 122 transmits light to cornea C from a selected one $132_1$ of the plurality of apertures, when selection aperture 122 is appropriately aligned with the selected one $132_1$ of the plurality of apertures. Subsequently, by translating second slit mask 120, the selection aperture can be positioned such that light from another of the plurality of apertures $132_n$ can be transmitted to cornea C. Such positioning of the selection aperture can be repeated such that light from each of the plurality of apertures or light from any suitable ones of the plurality of apertures 132 can be transmitted to cornea C. It will be appreciated that, on portions of the first slit mask and the second slit mask that are outside of the apertures disposed thereon, the slit masks are opaque or substantially opaque to light from source 12a.

It is to be appreciated that although, in the illustrated embodiment, the second slit mask 120 (i.e., the mask including the selection aperture) is disposed upstream (i.e., closer to source 12a along the optical path) from first slit mask 130, in other embodiments, the first slit mask (i.e., the mask including the plurality of apertures) can be disposed upstream of the second slit mask.

Referring again to FIG. 1, light sources 12a and 12b generate the light in which a corresponding mask subsystem is disposed. In some embodiments, the source projects light from the light sources in a cone of light CN to permit light to be projected through each of the apertures defined in first slit mask 130 without moving the source. That is to say that, in some embodiments, only the second slit mask 120 is moved.

The movement occurs to expose a given one of the plurality of apertures on the first mask 130 to light from a light source. It will be appreciated that, in such embodiments, the plurality of apertures 132 that provide the slits of light can remain fixed in a given location during the acquisition of the plurality of slit images used to produce a representation of a subject's eye. An advantage over prior art measurement apparatus, in which a single aperture is moved to produce slits of light, is that slits of light are produced with positions that are more accurately known, thereby providing more accurate representations of subjects' eyes.

In some embodiments, it is advantageous if the source is monochromatic and suitably bright. For example, an LED or a plurality of LEDs may be used to generate the light. In some embodiments, a high power LED has been found useful. In some embodiments, a superluminescent LED is used. An aspect of the invention is directed to a single high power LED configured and arranged to be capable of illuminating the plurality of apertures 132 as the selection aperture is moved.

In some embodiments, it is advantageous that the projection subsystem include a conventional condenser-projector system. In FIG. 1, condenser lenses 14a, 14b gather light from sources 12a and 12b respectively, and projector lenses 18a, 18b are configured and arranged such that the condenser lenses images sources 12a and 12b onto the projector lenses 18a, 18b, respectively. The projector lenses are also configured and arranged to image the apertures 132 onto cornea C. It is typically preferable that the slits of light are not convergent or divergent between the first slit mask and the cornea. However, some convergence or divergence may be present. Although in the illustrated embodiment the projector lenses 18a, 18b are conventional refractive lenses, any suitable imaging element may be used (e.g., a mirror, holographic element). In a given arm, a single lens may be fixed in a position to image all apertures onto the cornea. Alternatively, more than one lens may be positioned in the arm or a single lens may be moved to project the apertures.

Although in the illustrated embodiment the condenser lenses 14a, 14b are illustrated as conventional refractive lenses, any suitable imaging element may be used (e.g., a mirror, holographic element). In some embodiments, the condenser lens may be omitted. The projection system components and first slit mask 130 may be disposed in a Scheimpflug arrangement to obtain a plane of slit images at cornea C. Also, one or more folding mirrors 16a and 16b may be included to direct light onto the cornea, and to achieve an appropriate package shape to fit in a housing (not shown) of the apparatus.

Figure 3:
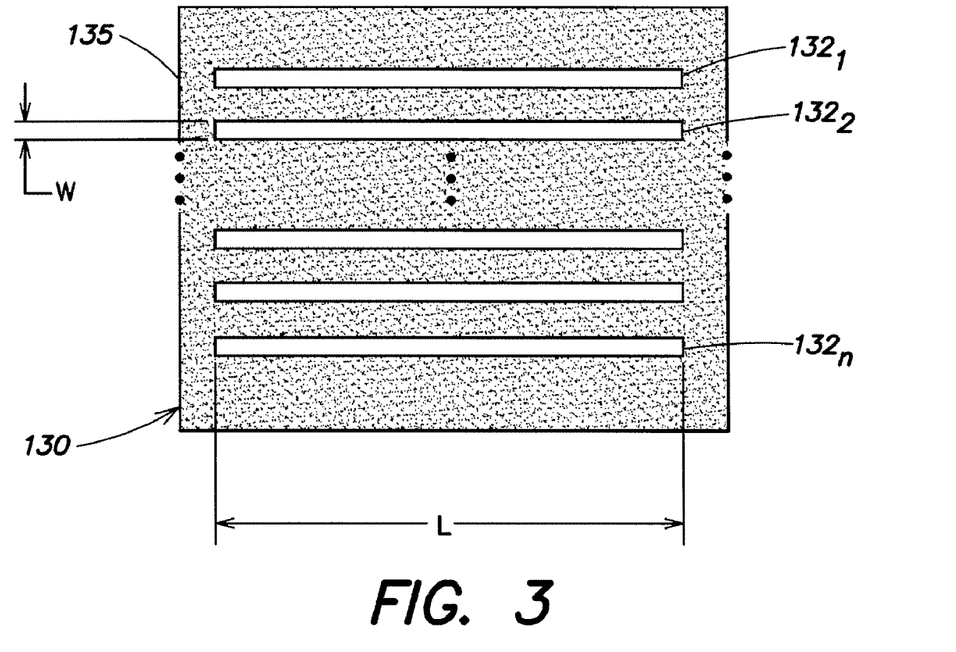
FIG. 3 is an illustration of an example of an embodiment of a first slit mask defining a plurality of apertures viewed along line 3-3 of FIG. 2.

Further details of first slit mask 130 are now given with reference to FIG. 3. Slit mask 130 includes a plurality of apertures $132_1$-$132_n$. Typically, the apertures are of a same width W and length L and are evenly spaced apart; however, aspects of the invention are not so limited.

For example, twenty apertures may be provided on the slit mask in first arm 75a (shown in FIG. 1) so that twenty slits of light are projected onto a subject's cornea and twenty images are obtained using light from the first arm 75a of the measurement apparatus 10 (shown in FIG. 1). Accordingly, when combined with twenty images from second arm 75b (shown in FIG. 1) a total of 40 slit images of a subject's eye are obtained. It will be appreciated that any suitable number of apertures may be provided on the first slit mask in each of mask subsystems 100a, 100b (shown in FIG. 1).

For example, first slit mask 130 may be formed on a substrate 135 of soda lime glass or BK7 glass. An opaque layer may be deposited on a surface of the substrate. For example, an opaque metal layer may be deposited on the substrate, and the apertures may be subsequently formed by etching a portion of the metal layer to expose the substrate. Each of the apertures is sized and shaped such that in a given measurement apparatus a slit of light is projected onto a cornea in a conventional manner. Typically, the apertures are rectangular in shape. However, any suitable shape may be employed. In some embodiments, it may be desirable to apply an antireflective coating to one or both of the surfaces of a substrate. Although the plurality of apertures 132 are shown as being formed on a single substrate (and in a single plane) any suitable construction may be used in which the apertures are formed at fixed locations relative to one another.

Figure 4:
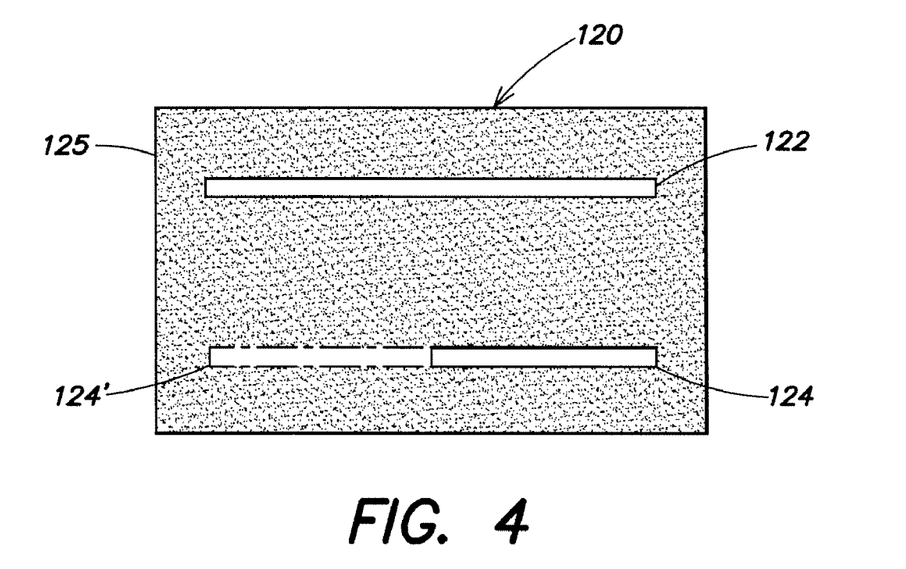
FIG. 4 is an illustration of an example of an embodiment of a second slit mask defining a selection aperture viewed along line 4-4 of FIG. 2.

Further details of the second slit mask 120 are now given with reference to FIG. 4. Slit mask 120 includes a single selection aperture formed on a substrate 125. The selection aperture is sized to permit light to pass from one of the plurality of apertures to cornea C (shown in FIG. 1). Typically, the size of the selection aperture is larger in width and length than any of the plurality of apertures. The selection aperture is also typically small enough such that light is only permitted to pass through a single one of the plurality of apertures and onto cornea C.

In the illustrated embodiment of the second slit mask, an aperture portion 124 (typically half the length of the selection aperture) is also provided. The aperture portion is used for alignment of the measurement apparatus relative to a subject's cornea on whom a corneal measurement is to be made. The aperture portion is aligned with one of the plurality of apertures on the first slit mask, such that light is projected though only a portion of the one of the plurality of apertures and a portion of a slit of light is projected onto the middle of a subject's eye by the first arm 75a (shown in FIG. 1) (e.g., an upper half of a slit is formed at the middle of the subject's eye by the first arm).

Another, second slit mask 120 also having an aperture portion is disposed in the other arm 75b (shown in FIG. 1). The position of aperture portion 124' in a second slit mask (in the second arm 75b) is shown in dashed lines. Similar, to the aperture portion in the first arm, the aperture portion in the second arm is aligned with one of the plurality of apertures on the first slit mask of the second arm. Again, the aperture is arranged to project light onto the middle of the subject's cornea (e.g., a lower half of an aperture is formed at the middle of the subject's eye). In a conventional manner, the subject's cornea is aligned with the measurement apparatus, by positioning either the subject or the machine such that the two portions of the slits of light align to form a single, full-length slit of light (e.g., the upper half of the slit of light from the first arm aligns with the lower half of the slit of light from the second arm) to form a single, full slit of light. The second slit masks 120 (in the first and second arm) may be formed in a manner similar to that described above for the first slit mask 130.

Referring again to FIG. 1, the image capture subsystem 50 is arranged to be able to capture an image of light projected for each of the plurality of apertures after the light impinges on the cornea. It will be appreciated that, to capture of the images to obtain a representation of a cornea, each of the plurality of apertures is selected sequentially by appropriately aligning each aperture with the selection aperture as described above. Image capture subsystem 50 may be any suitable conventional imaging device, such as a CCD camera.

Movement apparatus 110 may comprise any suitable mechanism for moving (e.g., translating) the second mask 120 to project slits of light form the plurality of apertures 132 on the first slit mask 130 to cornea C. For example, the movement apparatus may comprise a linear translation motor capable of the moving (i.e., translating) the second slit mask in a direction perpendicular to the length L of the plurality of apertures 132.

Corneal measurement apparatus 10 also includes an image processing subsystem to convert the images into a single representation of the cornea. Techniques for reconstructing a representation of a subject's cornea once the slit images are obtained are well known and are not described further here. Projection systems as described herein may be used with corneal topographers, corneal profiler apparatus and anterior chamber analyzers.

Corneal measurement apparatus 10 includes a subject positioning apparatus 60 adapted to maintain a subject's cornea in a location. For example, the apparatus may be provided with a chin rest and/or a forehead rest which will fix the location of the subject's head.

Figure 5:
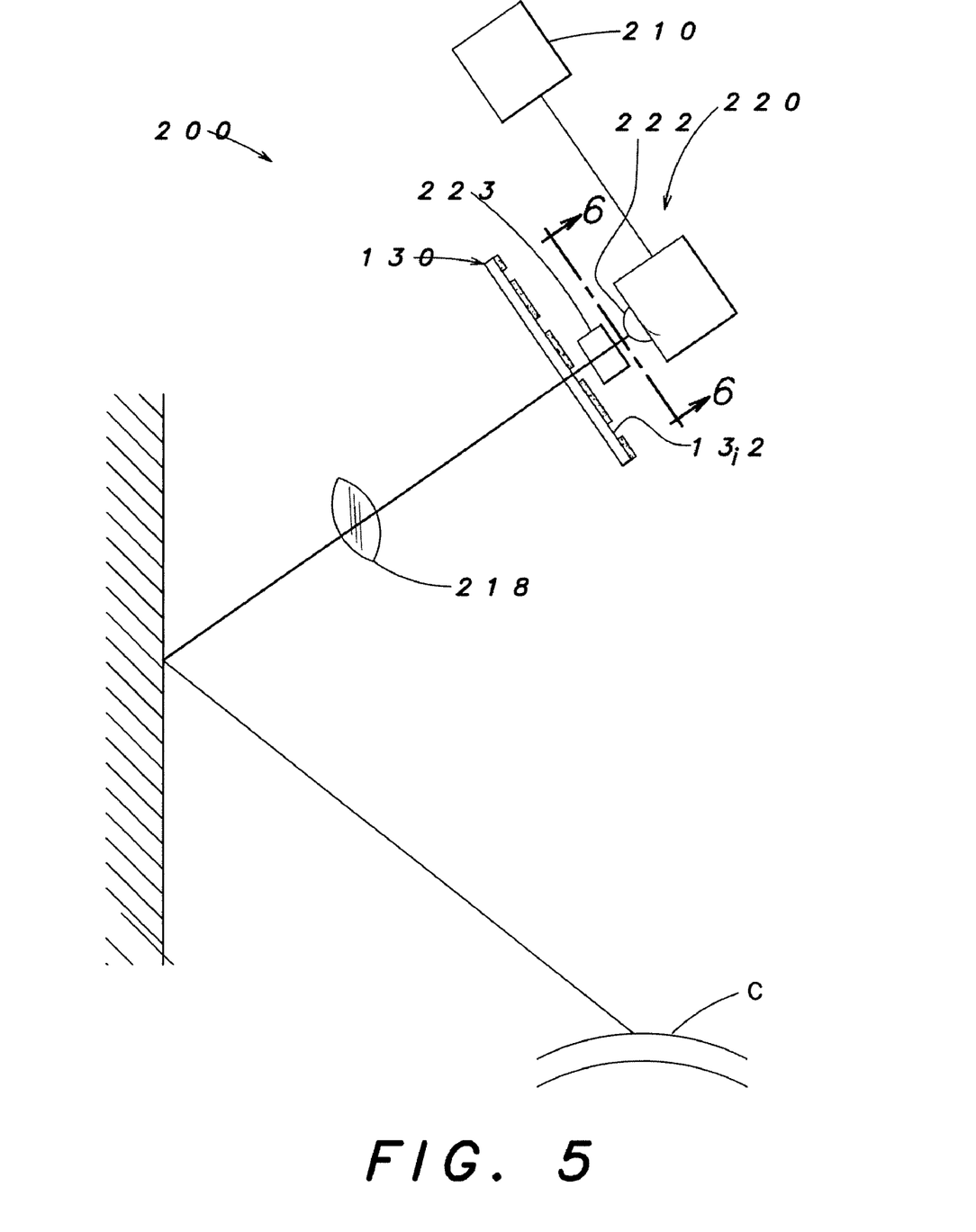
FIG. 5 illustrates further details of another example of an embodiment of one arm of the corneal measurement apparatus shown in FIG. 1.

FIG. 5 illustrates further details of another example of an embodiment of one arm 200 of corneal measurement apparatus 10 (shown in FIG. 1). The arm comprises a mask subsystem comprising first slit mask 130 defining a plurality of apertures $132_i$; and a slit projection subsystem 220 comprising a plurality of light sources $212_{1-n}$ (shown in FIG. 6). It will be appreciated that, in contrast to the embodiment shown in FIG. 2, subsystem 220 is arranged to project a slit of light without the use of a mask having a selection aperture (e.g., mask 120 having a selection aperture 122 in FIG. 2). In some embodiments, the projection subsystem comprises a cylindrical lens 222 to gather light from the light sources and focus it on a selected one of the apertures $132_i$. Alternative arrangements for projecting a slit of light are given in U.S. Pat. No. 6,409,346 (issued Jun. 25, 2002) and U.S. Pat. No. 6,286,958 (issued Sep. 11, 2001) both to Koest. Additionally, a prism 223 may be located in the path of the slit of light to improve homogeneity of the light, the prism being rotated or oscillated as taught in U.S. Pat. No. 7,040,765 (issued May 9, 2006). The substance of said three (3) patents is hereby incorporated by reference.

The arm also comprises a movement apparatus 210 adapted to move (e.g., translate) the slit projector subsystem 220, so as to appropriately position the plurality of light sources such that light travels through a selected one of the plurality of apertures $132_i$ and is focused onto cornea C (e.g., by lens 218).

Figure 6:
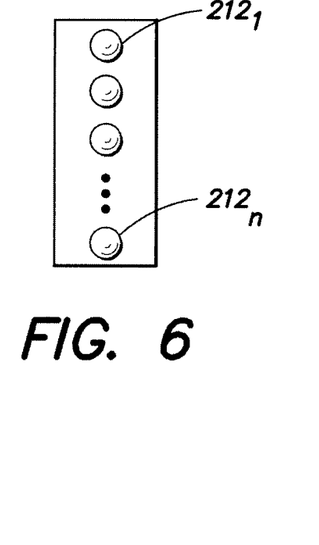
FIG. 6 is a schematic illustration of further details of one example of light sources included in a slit projection subsystem.

FIG. 6 is a schematic illustration of the further details of the light sources $212_{1-n}$ included in the illumination slit projection subsystem. The sources may, for example, comprise LEDs disposed on a circuit board to project a long narrow band of light. Any suitable number LEDs may be used. Although, a plurality of sources is shown in the illustrated embodiment, a single elongate source may be used.

Figure 7:
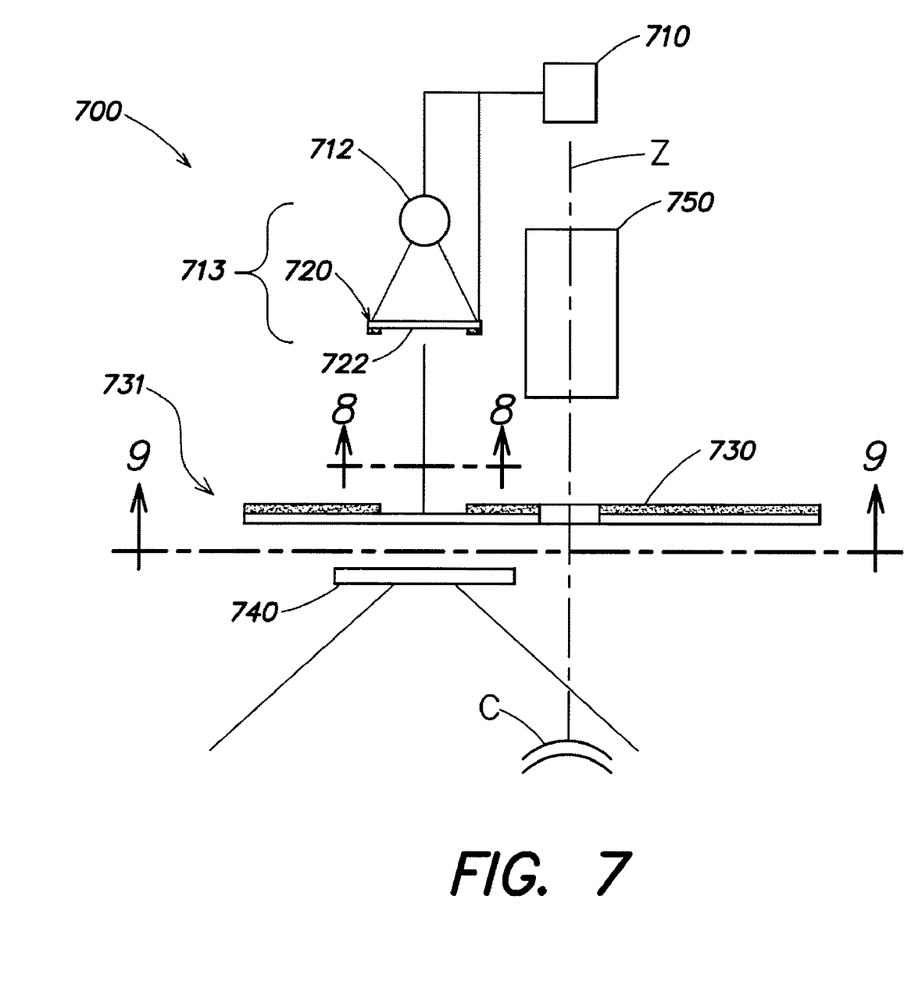
FIG. 7 is a schematic view of another example of a corneal measurement apparatus according to aspects of the present invention.

FIG. 7 is a schematic view of another example of a corneal measurement apparatus 700 according to aspects of the present invention. The corneal measurement apparatus comprises a slit projection systems 713 (including a light source 712), a mask subsystems 731, and an image capture subsystem 750. The mask subsystem is disposed in the path of light from slit projection systems 713. The mask subsystem comprises a first slit mask 730 defining a plurality of apertures $732_{1-n}$ (shown in FIG. 9).

Slit projection systems 713 comprises a light source 712, a second slit mask 720 defining a selection aperture 722 (shown in FIG. 8), and a slit imaging lens 740 (e.g., a cylindrical lens having a length aligned with the length of the selection aperture). Slit projection systems 713 also comprises a movement apparatus 710 adapted to rotate source 712 and second mask 720. By appropriately positioning the second slit mask using the movement apparatus, selection aperture 722 selectively transmits portions of the light from source 712 such that light traveling through a selected one of the plurality of apertures $732_i$ impinges on cornea C. As discussed above, in some embodiments, the source may project a cone of light such that movement of the source is not necessary to project a plurality of slits of light.

In some embodiments, imaging lens 740 is rotated by movement apparatus along with source 712 and second mask 720; alternatively, a plurality of imaging lenses can be arranged such that one is aligned with each of the plurality of apertures of first slit mask 730. It will be appreciated that, in embodiments as illustrated in FIG. 7, the plurality of apertures 732 that provide the slits of light can remain fixed in a given location during the acquisition of the plurality of slit images used to produce a representation of a subject's eye. An advantage over prior art measurement apparatus is that slits of light are produced with positions that are more accurately known than with conventional apparatus, thereby providing more accurate representations of subjects' eyes.

Figure 8:
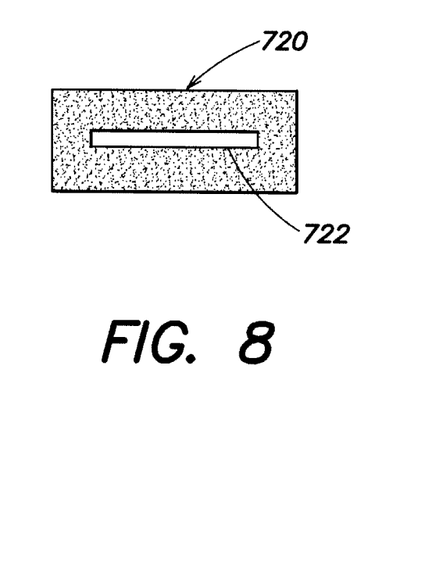
FIG. 8 is an illustration of an example of an embodiment of a second slit mask defining a selection aperture viewed along line 8-8 of FIG. 7.
Figure 9:
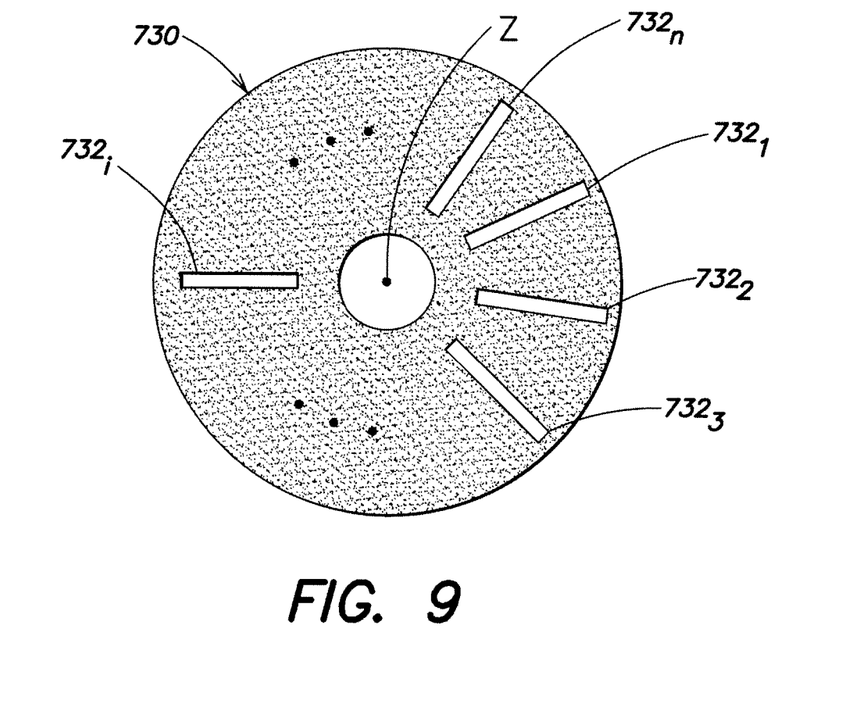
FIG. 9 is an illustration of further details of an example of an embodiment of first slit mask defining a plurality of apertures viewed along line 9-9 of FIG. 7.

FIG. 8 is an illustration of an example of an embodiment of a second slit mask 720 defining a selection aperture 722 viewed along line 8-8 of FIG. 7. FIG. 9 is an illustration of further details of an example of an embodiment of first slit mask 730 defining a plurality of apertures $732_i$ viewed along line 9-9 of FIG. 7. It will be appreciated that, in some embodiments, slit projection system 713 comprises a source as in FIG. 2; and in other embodiments, slit projection system 713 is constructed as slit projection system 220 (shown in FIG. 6) and as such comprises a source or sources configured to project a slit of light without the use of a selection aperture.

Having thus described the inventive concepts and a number of exemplary embodiments, it will be apparent to those skilled in the art that the invention may be implemented in various ways, and that modifications and improvements will readily occur to such persons. Thus, the embodiments are not intended to be limiting and presented by way of example only. The invention is limited only as required by the following claims and equivalents thereto.

What is claimed is:

1. An apparatus for measuring a subject's cornea, comprising:

(A.) a slit beam projection subsystem comprising a light source;

(B.) a mask subsystem disposed in a path of light from the light source, comprising a first slit mask defining a plurality of apertures;

(C.) a movement apparatus adapted to move at least a portion of the slit projection subsystem to transmit light through each of the plurality of apertures while maintaining the plurality of apertures in a fixed location, the movement apparatus configured and arranged such that, by moving the portion of the slit beam projection subsystem, portions of the light can be selectively transmitted through only one aperture of the plurality of apertures at a time toward the cornea;

(D.) an imaging element configured and arranged to image at least one of the plurality of apertures onto the cornea; and (E.) an image capture subsystem arranged to capture images of the portions of light after the light impinges on the cornea.

2. The apparatus of claim 1, wherein the slit beam projection subsystem comprises a second slit mask defining a selection aperture, the movement apparatus being adapted to move the second slit mask.

3. The apparatus in claim 1, further comprising
(F.) a second slit beam projection subsystem comprising a second light source;
(G.) a second mask subsystem disposed in a path of second light from the second slit projection subsystem, comprising a second slit mask defining a second plurality of apertures;
(H.) a second movement apparatus adapted to move at least a portion of the second slit projection subsystem, the second movement apparatus configured and arranged such that by moving the portion of the second slit beam projection subsystem, portions of the second light can be selectively transmitted through an aperture of the second plurality of apertures toward the cornea; and
(I.) a second imaging element configured and arranged to image the second plurality of apertures onto the cornea, the image capture subsystem arranged to capture images of the portions of second light after the light impinges on the cornea.

4. The apparatus in claim 2, wherein the second slit mask is disposed upstream of the first slit mask.

5. The apparatus in claim 1, wherein the slit beam projection subsystem is configured and arranged to project light from the light source through each of the plurality of apertures defined in the first slit mask without moving the light source.

6. The apparatus in claim 1, wherein the light source comprises at least one LED arranged to project light in the path of light.

7. The apparatus in claim 1, further comprising a condenser lens configured and arranged to gather light from the light source and project the light in the path of light.

8. The apparatus in claim 7, wherein the imaging element and condenser lens are configured and arranged to operate as a condenser-projector system.

9. The apparatus in claim 1, wherein the imaging element and the first slit mask are disposed in a Scheimpflug arrangement to obtain a plane of slit images at the cornea.

10. The apparatus in claim 1, wherein the plurality of apertures are disposed in a single plane.

11. The apparatus in claim 1, wherein the plurality of apertures are formed on a single substrate.

12. The apparatus in claim 11, wherein the plurality of apertures is defined by openings in an opaque layer deposited on the substrate.

13. The apparatus in claim 1, further comprising an image processing subsystem coupled to the image capture subsystem, the image processing subsystem being adapted to convert the images into a representation of the cornea.

14. The apparatus in claim 1, further comprising a subject positioning apparatus adapted to maintain the subject's cornea in a location.

15. The apparatus in claim 6, wherein the light source comprises at least one high power LED.

16. The apparatus in claim 5, wherein the light source consists of a single LED.

17. The apparatus of claim 1, wherein the movement apparatus is adapted to translate the at least portion of the slit projection subsystem.

18. The apparatus of claim 17, wherein the light source is adapted to project a slit of light and the movement apparatus is adapted to translate the light source.

19. The apparatus of claim 2, wherein the movement apparatus is adapted to translate the second slit mask.

20. The apparatus of claim 1, wherein the movement apparatus is adapted to rotate the at least portion of the slit projection subsystem.

21. A method of facilitating measurement of a subject's cornea, comprising:
(A.) providing a plurality of apertures;
(B.) projecting light toward the plurality of apertures;
(C.) moving at least a portion of a slit beam projector subsystem while maintaining the plurality of apertures in fixed locations to selectively transmit a portion of the light toward the cornea, the portion of the light passing through only one aperture of the plurality of apertures;
(D.) imaging the portions of light after the light impinges on the cornea to produce images; and
(E.) processing the images to convert the images into a representation of the cornea.

22. The method of claim 21, where the step of moving comprises translating the at least portion of the slit beam projection subsystem.

23. The method of claim 21, where the step of moving comprises rotating the at least portion of the slit beam projection subsystem.

24. The method of claim 21, where the moving comprises moving a selection aperture that is distinct from the plurality of apertures.

25. The method of claim 21, where the moving comprises moving at least one light source.

26. The method of claim 24, wherein the light passes through the selection aperture prior to passing through any of the plurality of apertures.

27. The method of claim 21, wherein the step of projecting light comprises projecting light from at least one LED.

* * * * *